United States Patent [19]

Bolton et al.

[11] Patent Number: 5,256,411

[45] Date of Patent: * Oct. 26, 1993

[54] IMMUNE CELL PROLIFERATION INHIBITORS

[75] Inventors: Anthony E. Bolton, Sheffield, United Kingdom; Alan Drizen, Downsview, Canada

[73] Assignee: Intermune Life Sciences, Inc., Ontario, Canada

[*] Notice: The portion of the term of this patent subsequent to Aug. 13, 2008 has been disclaimed.

[21] Appl. No.: 720,591

[22] Filed: Jun. 28, 1991

Related U.S. Application Data

[63] Continuation-in-part of Ser. No. 295,734, Jan. 11, 1989, Pat. No. 5,039,521.

[51] Int. Cl.$^5$ .................... A61K 39/395; A61K 37/00
[52] U.S. Cl. ......................................... 424/85.8; 514/2
[58] Field of Search ........................... 514/2; 424/85.8

[56] References Cited

U.S. PATENT DOCUMENTS

| | | | |
|---|---|---|---|
| 4,705,687 | 11/1987 | Lau | 424/95 |
| 4,748,246 | 5/1988 | Skotnicki et al. | 544/331 |
| 4,751,305 | 6/1988 | Skotnicki et al. | 544/331 |
| 4,752,578 | 6/1988 | Moore et al. | 435/68 |
| 4,766,069 | 8/1988 | Auron et al. | 435/70 |

OTHER PUBLICATIONS

Pockley, A. G., "An Investigation Into the Immunomodulatory Activities of Human Placental Protein 14 (PP14)," Chem. Abst., vol. 111 (1989).
Pockley et al., "Placental Protein 14 (PP14) Inhibits the Synthesis of Interleukin-2 and the Release of Soluble Interleukin-2 Receptors from the Phytohaemagglutinin-stimulated Lymphocytes," Clin. Exp. Immunol. (1989) 77, pp. 252-256.
Bolton et al., "The Radioimmunassay of Human Placental Protein 14 (PP14)", Clinica Chimica Acta, 135 (1983), pp. 283-291.
A. G. Pockley, et al., "Suppression of In Vitro Lymphocyte Reactivity to Phytohemagglutinin by Placental Protein 14," Journal of Reproductive Immunology, vol. 13, 1988, pp. 31-39.
A. E. Bolton et al., "Identification of Placental Protein 14 as an Immunosuppressive Factor in Human Reproduction," The Lancet, Mar. 14, 1987, pp. 593-595.
M. Julkunen et al., "Complete Amino Acid Sequence of Human Placental Protein 14: A Progesterone-Regulated Uterine Protein Homologous to Beta-Lactoglobulins," Proc. Natl. Acad. Sci. U.S.A., vol. 85, Dec. 1988, pp. 8845-8849.
Pockley et al., "The Effect of Human Placental Protein 14 (PP14) on the Production of Interleukin-1 from Mitogenically Stimulated Mononuclear Cell Cultures," Immunology (1990) 69, pp. 277-281.

*Primary Examiner*—Sam Rosen
*Attorney, Agent, or Firm*—Mason, Fenwick & Lawrence

[57] ABSTRACT

A method for treating an immune system disorder in a human by administering to the human a therapeutically effective amount of an active substance selected from the group consisting of PP14, derivatives of PP14, muteins of PP14, fragments of PP14, and subunits of PP14, to alleviate the immune system disorder.

28 Claims, 1 Drawing Sheet

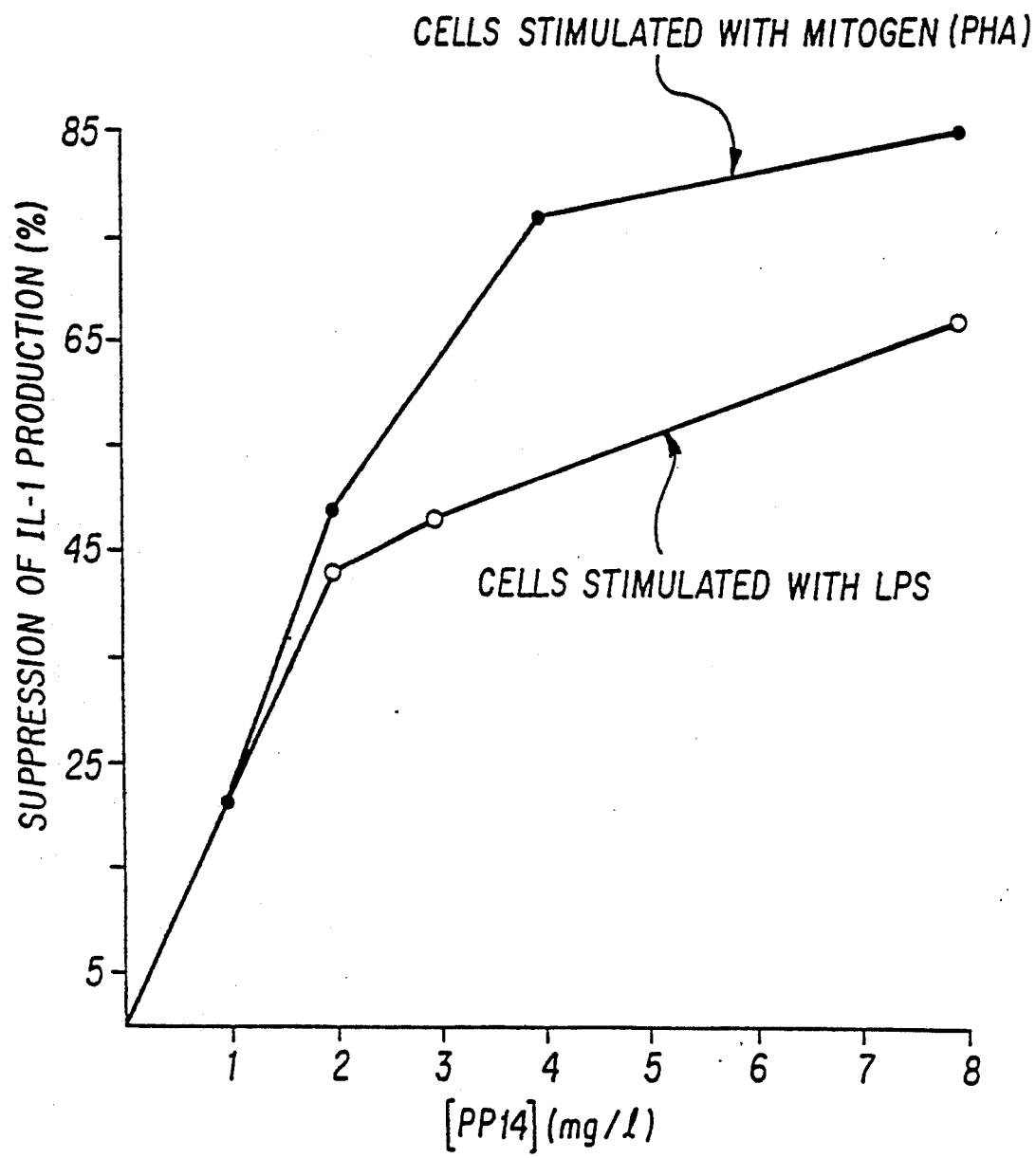

IMMUNE CELL PROLIFERATION INHIBITORS

RELATED APPLICATION

The present application is a continuation-in-part application of U.S. patent application Ser. No. 295,734, filed Jan. 11, 1989, now U.S. Pat. No. 5,039,521 the entire disclosure of which is incorporated herein by reference.

BACKGROUND OF THE INVENTION

1. Field of the Invention

The present invention relates to inhibitors of immune cell proliferation and function. More particularly, the present invention is directed to the use of PP14 as an inhibitor of immune cell proliferation and function.

2. Background of the Invention

The human immune system functions to protect the organism from infection and from foreign antigens by cellular and humoral mechanisms. The immune system consists of a complex organization of many types of lymphocytes, and macrophage or other antigen-presenting cells. These agents regulate each other by means of multiple cell-cell interactions and by elaborating soluble factors, including lymphokines and antibodies, that have autocrine, paracrine, and endocrine effects on immune cells. Disorders of the regulation of this system may result in the uncontrolled proliferation of immune cells and eventually to malignancy, uncontrolled response to foreign antigens or organisms leading to allergic or inflammatory diseases, aberrant immune responses directed against host cells leading to organ damage and dysfunction, or generalized suppression of the immune response leading to severe and recurrent infections.

Interleukin 1 (IL-1) is a peptide cytokine secreted by a variety of cell types including accessory cells of the immune system, and the antigen presenting cells. Interleukin 1 has a variety of functions including an involvement in the activation of immune system T cells. Cells secreting IL-1 include monocytes present in the circulating blood, macrophages found in interstitial fluid, and dendritic cells.

It now appears established that IL-1 is a central mediator of inflammatory reactions and is important in the pathogenesis of chronic inflammatory diseases, of which rheumatoid arthritis (RA) is one example. Evidence of this function of IL-1 has been derived from a variety of experimental approaches and may be summarized as follows:

1. Prostaglandins and leukotrienes are mediators of inflammatory reactions; hence non-steroidal anti-inflammatory drugs, which inhibit cyclooxygenase and prostaglandin synthesis, are useful therapeutically in such conditions. IL-1 mobilizes free arachidonate, the precursor of prostaglandins and leucotrienes, by activating phospholipase, and also induces cyclooxygenase.

2. IL-1 stimulates binding of T-cells to endothelial cells, thought to be the first step in their influx into joints.

3. Injection of recombinant IL-1 into joints causes an influx of inflammatory cells, followed by a loss of proteoglycan from the cartilage.

Treatment of allergies and autoimmune diseases has been based on modalities which are toxic to immune cells, that inhibit production of antibodies, or inhibit the effects of mediators of the immune response, such as histamine. Over the past several years many soluble lymphokines which regulate the immune system have been characterized. Drugs which allow manipulation of the production or function of such factors would be of use in the treatment of autoimmune diseases and perhaps in the treatment of diseases resulting from the uncontrolled proliferation of immune cells.

It is now becoming widely accepted that IL-1 (both IL-1 alpha and IL-1 beta) are important mediators of inflammatory responses. IL-1 appears to directly cause cartilage breakdown in knee joints, and may be central in the pathogenesis of rheumatoid arthritis. An inhibitor may, therefore, be of importance in treatment of this disease. It is of interest that placental protein 14 (PP14) is a natural product present at elevated levels in the peripheral circulation early in pregnancy, peaking around week 9-10. There are reports in the literature that there is a marked improvement in some sufferers of rheumatoid arthritis in the first trimester of pregnancy. Similar reports of an improvement in patients with chronic asthma during the first trimester of pregnancy can also be found in the published literature. Chronic asthma is an inflammatory disease, and although IL-1 has not yet been implicated in its etiology, this remains a possibility.

As PP14 appears early in pregnancy, it may be associated with the process of implantation, and in maintaining the early conceptus which may be particularly prone to immune rejection by the maternal immune system. It is possible that PP14 could be of utility in the treatment of early miscarriage, which may relate to immune phenomena.

Pregnancy is a normal state in which at least one aspect of the immune response—reaction to foreign antigens—is suppressed with regard to paternal antigens expressed by the fetus. It is rational, therefore, to seek natural inhibitory regulators of the immune response in the tissue or bloodstream of pregnant women. A variety of proteins are expressed at high levels during pregnancy. One of these, PP14, is a major secretory protein of decidual tissue, where it comprises about 10% of the total soluble protein.

SUMMARY OF THE INVENTION

The present invention is directed to a method for treating an immune system disorder in a human by administering to the human an active substance selected from the group consisting of PP14, derivatives of PP14, muteins of PP14, fragments of PP14, and subunits of PP14, in an amount effective to alleviate the disorder. The disorders which may be treated by this method include allergic conditions, autoimmune conditions, and inflammatory conditions.

The active substance may be administered to the patient by any appropriate route, including intravenous injection, intramuscular injection, oral administration, topical administration, rectal administration, and inhalation. The active substance may be administered in admixture with a pharmaceutically acceptable carrier.

The active substance may be obtained from a variety of sources, including mammalian placenta, mammalian blood, amniotic fluid, seminal plasma, cells in tissue culture, decidual cells, decidual organs, endometrial cells, endometrial organs, and recombinant protein sources.

Specific immune system disorders which may be treated according to this method include arthritis, rheumatoid arthritis, asthma, graft-versus-host disease, organ rejection, osteoarthritis, systemic lupus erythematosus, atopic allergy, multiple sclerosis, allergic dermatitis, inflammatory bowel disease, psoriasis, sarcoidosis, and other inflammatory disorders.

The immune system disorder to be treated according to the present invention may be a lymphoproliferative disorder, such as malignant non-Hodgkin's lymphoma, Hodgkin's disease, or malignant histiocystosis. Also, the immune system disorder may be a neoplastic disorder, such as a leukemia.

The discoveries of the present invention may also be applied to test inflammatory and autoimmune diseases, and may be applied to treat autoimmune diseases manifested by infertility. The immune system disorder to be treated may be a disorder resulting from the presence in the human of the virus which causes acquired immunodeficiency syndrome.

The present invention is also directed to a method for treating an immune system disorder in a human by administering to the human monoclonal antibodies directed against a substance selected from the group consisting of PP14, derivatives of PP14, muteins of PP14, fragments of PP14, and subunits of PP14.

The monoclonal antibodies may be administered by a method selected from the group consisting of intravenous injection, intramuscular injection, oral administration, topical administration, rectal administration, and inhalation, and may be administered in admixture with a pharmaceutically acceptable carrier.

The present invention extends to a composition of matter comprising monoclonal antibodies directed against a substance selected from the group consisting of pp14, derivatives of PP14, muteins of PP14, fragments of PP14, and subunits of PP14. The monoclonal antibodies may be specifically directed against PP14.

In another embodiment of the invention, a hybridoma cell line producing such monoclonal antibodies is provided.

In a further embodiment, the present invention is directed to a method for the detection and quantification of PP14, the method which comprises:

(a) contacting a sample suspected of containing PP14 with the composition in accordance with the present invention; and (b) subjecting the sample to an assay to detect the presence and amount of any antibody-antigen reaction therein.

The assay may be selected from the group consisting of radioimmunoassay, ELISA assays, and immunoblotting assays.

The present invention further includes a method for purifying PP14 from a substance containing PP14, the method which comprises contacting the substance with monoclonal antibodies directed against the PP14, whereby an immuno-precipitation reaction, or antigen: antibody interaction results.

DETAILED DESCRIPTION OF THE INVENTION

Of the range of proteins which are known to be associated with the pregnancy state, one has been found to exhibit an immunosuppressive activity in a variety of in vitro tests. Further investigation of the mode of action of this peptide, PP14, has indicated that it inhibits IL-1 production by peripheral white blood cells (containing both T-lymphocytes and monocytes) after stimulation. The concentration at which PP14 is active appears to be the levels at which it is found normally during pregnancy. The time course of this inhibition of IL-1 production closely relates to the immunosuppressive activity of the molecule, indicating that its primary effect is on monocytes rather than other immune system cells.

The pregnancy-associated protein, PP14, has been found to inhibit IL-1 production by stimulated macrophages and to inhibit monocytes lymphokine secretion, IL-2 receptor expression and proliferation of mitogen or allogeneically stimulated lymphocytes.

Treatment of autoimmune, allergic, inflammatory, or lymphoproliferative disorders may thus be effected by administration of PP14 of to patients. Administration of PP14 according to the invention therefore provides a new modality for the treatment of these disorders.

Specific immune system disorders which may be treated according to the invention include arthritis, rheumatoid arthritis, asthma, graft-versus-host disease, organ rejection, osteoarthritis, systemic lupus erythematosus, atopic allergy, multiple sclerosis, allergic dermatitis, inflammatory bowel disease, psoriasis, sarcoidosis, and other inflammatory disorders.

The immune system disorder to be treated according to the present invention may be a lymphoproliferative disorder, such as malignant non-Hodgkin's lymphoma, Hodgkin's disease, or malignant histiocystosis.

As indicated above, the discoveries of the present invention may also be employed to treat autoimmune diseases manifested by infertility. The immune system disorder to be treated may be a disorder resulting from the presence in the human of the virus which causes acquired immunodeficiency syndrome. In addition, the immune system disorder may be a neoplastic disorder, such as leukemia.

The PP14 active substance utilized in the inventive method may be obtained from a variety of sources, including mammalian placenta, mammalian blood, amniotic fluid, seminal plasma, cells in tissue culture, decidual cells, decidual organs, endometrial cells, endometrial organs, as well as recombinant protein sources, including sources containing eukaryotic cells or prokaryotic cells engineered to express PP14, muteins of PP14, fragments of PP14 or subunits of PP14.

The present invention is also directed to a method for treating an immune system disorder in a human by administering to the human monoclonal antibodies directed against a substance selected from the group consisting of PP14, derivatives of PP14, muteins of PP14, fragments of PP14, and subunits of PP14.

A monoclonal antibody directed against PP14 has been isolated. This antibody is used to detect and to quantitate in vivo levels of PP14. Administration of the antibody to mammals may neutralize physiologic and pathophysiologic actions of PP14.

The monoclonal antibodies may be administered by a method selected from the group consisting of intravenous injection, intramuscular injection, oral administration, topical administration, rectal administration, and inhalation, and may be administered in admixture with a pharmaceutically acceptable carrier.

The present invention therefore also extends to a composition of matter comprising monoclonal antibodies directed against a substance selected from the group consisting of PP14, derivatives of PP14, muteins of PP14, fragments of PP14, and subunits of PP14. The monoclonal antibodies may be specifically directed against PP14.

Another aspect of the present invention is the isolation of a monoclonal antibody to PP14 which can be utilized for the detection and quantitation of PP14. Such an antibody can also be used to facilitate efficient purification of the factor. Inhibition of PP14 activity by binding it to an antibody can be used in vitro to study its cellular and biochemical effects, and in vivo in animals to study its effects on mammalian biology. Disorders in which the immune response is abnormally suppressed or attenuated may be potentially treated by inhibiting PP14 activity with such an antibody.

In yet another embodiment of the present invention, a hybridoma cell line producing such monoclonal antibodies is provided. Further, the present invention is directed to a method for the detection and quantification of PP14, comprising the steps of:

(a) contacting a sample suspected of containing PP14 with the composition in accordance with the present invention; and (b) subjecting the sample to an assay to detect the presence and amount of an antibody:antigen reaction therein.

The present invention defines the immunoregulatory properties of PP14, and describes a method for using these properties in the treatment of autoimmune, inflammatory, allergic and neoplastic disorders of humans and other mammals. Without wishing to be bound by any particular theory, the chemical structure and immunoregulatory properties of PP14 in suppressing lymphokine secretion and lymphoproliferative disorders will be described in relation to the present invention.

PP14 has been found to inhibit mitogenic stimulation of proliferation and secretion of interferon and IL-2 by lymphocytes. A similar inhibition of allogeneic stimulation of lymphocytes has also been measured. These effects have been found to be accompanied by a reduction in the affinity of high affinity lymphocyte IL-2 receptors and an inhibition of the expression of functional IL-2 receptors.

PP14 suitable for purposes of the present invention is found in extracts of human decidual tissue; the material binds to the monoclonal antibody used in accordance with the present invention. The activities observed from in vitro test systems correlate with the PP14 content of tissue extracts and other preparations, as measured in a radioimmunoassay for PP14 that utilizes a polyclonal antibody. This radioimmunoassay is described in the publication by Anthony E. BOLTON et al., entitled "The Radioimmunoassay of Human Placental Protein 14 (PP14)," *Clinica Chimica Acta*, 135 (1983) 283-291. The PP14 suitable for purposes of the present invention has been observed to be functional in the inhibition of the proliferation of mitogen and allogeneically stimulated peripheral blood mononuclear cells; the inhibition of the production and/or release of IL-1 by stimulated peripheral blood mononuclear cells; and the reduction in the affinity of binding of IL-2 to stimulated peripheral blood mononuclear cells.

Activation of the immune regulatory and proliferative capacity of lymphocytes is a complex process mediated by a number of lymphokines and requiring the cooperation of accessory cells. These cells secrete the lymphokine IL-1 in response to antigenic stimulation. This factor is required for the expression of the IL-2 receptor by lymphocytes which then respond mitogenically to IL-2.

PP14 inhibits the elaboration of IL-1 by activated or stimulated peripheral blood monocytes; this may account for many of the modulating activities of PP14. Similar suppressive effects are induced by crude decidual extracts; this activity is abolished by an antibody to PP14. Thus, PP14 has been discovered to have immunosuppressive activity related to its ability to decrease expression or secretion of IL-1 and possibly independent effects on lymphocyte secretion and proliferation.

Many human diseases result from an abnormal, unregulated proliferation of lymphocytes, or from an uncontrolled immune response directed against the patient's own cells or tissues. Some of these defects may result from elevated, unregulated secretion of lymphokines. An example is rheumatoid arthritis, in which IL-1 has been shown to activate synovial prostaglandin and leukotriene production, enhance T-cell binding to endothelia, and to reproduce several aspects of the condition in animal models. Similar evidence exists for other chronic inflammatory diseases. PP14, an inhibitor of IL-1 production, is a potential treatment modality for such diseases, including syndromes such as asthma, which is characterized by excessive secretion of leukotrienes in the bronchial tree, and allergic dermatitis and inflammatory bowel diseases, which are characterized by chronic overproduction of mediators of inflammation.

Other autoimmune diseases, such as systemic lupus erythematosus, Sjogren's syndrome, and scleroderma are characterized by abnormal ratios of a variety of different types of T- and B- lymphocytes which may result from defective regulation of their proliferation. More extreme losses of regulation of growth may be accompanied by further genetic changes in the cells and result in overgrowth of a malignant clone of cells leading to a malignancy in the patient. Such malignant cells often still require autocrine or paracrine stimulation by a lymphokine growth factor in order to drive their proliferation.

Inhibition of expression of these factors or of their receptors by PP14 provides an effective mode for treatment of these patients according to the invention. The precise physiologic role and regulation of PP14, and whether it ever functions or is expressed abnormally in human disease, is unknown.

The present invention is based on the discovery that placental protein 14, or other therapeutically active forms thereof, may be employed to treat human immune system disorders. Useful forms of PP14 for purposes of the present invention include natural and recombinant forms of PP14 itself, as well as derivatives, muteins, fragments, and subunits of PP14, provided that the desired therapeutic activity of the substance is maintained.

PP14 is a glycoprotein comprising about 17.5% carbohydrate content. The details of this carbohydrate content are not presently known; however, PP14 binds strongly to the lectin concanavalin-A, which is known to have an affinity for terminal alpha-D-mannosyl and alpha-D-glucosyl residues, as well as to wheat germ agglutinin, which has an affinity for N-acetyl-beta-D-glucosaminyl residues. The presence of the latter is further evidenced by the reduction of the interaction of PP14 with specific antibodies caused by treatment of PP14 with the enzyme beta-N-acetyl glucosaminidase, which removes these residues.

The nucleotide and amino acid sequence of PP14 cDNA, as deduced by Julkunen et al., is shown in the accompanying Sequence Description (SEQ ID NO:1). The entire disclosure of Julkunen et al., "Complete Amino Acid Sequence of Human Placental Protein 14: A Progesterone-Regulated Uterine Protein Homologous to β-lactoglobulins," *Proc. Natl. Acad. Sci. USA*, Vol. 85, pp. 8845-8849, December 1988, is incorporated herein by reference.

It will be understood that the precise chemical structure Of PP14 depends upon a number of factors. For example, since ionizable amino and carboxyl groups are present in the molecule, a particular protein may be obtained as an acidic or basic salt, or in neutral form. All forms of PP14 which retain their therapeutic activity for purposes of the instant invention are intended to be within the scope of the definition of "PP14".

It should be noted that the N-terminal amino acid sequence of PP14 shows substantial sequence homology with certain animal β-lactoglobulins, but the biological activities of these proteins are not well understood. Furthermore, there is some sequence homology between PP14 and human serum retinol binding protein.

The term "recombinant" used herein refers to PP14 produced by recombinant DNA techniques wherein the gene coding for the PP14 is cloned by known recombinant DNA technology. For example, the human gene for PP14 may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host.

Therapeutically useful derivatives of PP14 may be prepared by augmenting the primary amino acid sequence of the protein PP14 with at least one additional molecule selected from the group consisting of qlucose moieties, lipids, phosphate groups, acetyl groups, hydroxyl groups, saccharides, methyl groups, propyl groups, amino acids, and polymeric molecules. Augmentation may be accomplished through post-translational processing systems of the producing host, or it may be carried out in vitro. Both techniques are well-known in the art.

Referring to the Sequence Description of PP14, it should be noted that the peptide includes three potential glycosylation sites at amino acid residues 28-30, 63-65, and 85-87. Glycosylation is a process of forming a protein derivative, wherein a portion of the protein's amino acid sequence is augmented by a sugar moiety. It will therefore be understood that therapeutically useful derivatives of PP14 may be prepared by addition of one or more sugar residues to the protein, or alternatively by removal of some or all of the sugar residues from the sites of glycosylation on the PP14 molecule.

Other therapeutically useful derivatives of PP14 may be formed by modifying at least one amino acid residue of PP14 by oxidation, reduction, or other derivatization processes known in the art.

Muteins of PP14 which do not destroy the activity of the protein may be used as the active treating substance of the instant invention. Muteins are prepared by modification of the primary structure of the protein itself, by deletion, addition, or alteration of the amino acids incorporated into the sequence during translation. For example, at least one cysteine residue of PP14 may be replaced with a conservative amino acid, in order to eliminate sites of undesirable intramolecular disulfide bond formation. Crosslinking is undesirable if it changes the conformation of PP14 so as to render the protein essentially inactive for purposes of treating an immune system disorder. Also, it may be desirable to replace a methionine which is not essential to bioactivity with a conservative amino acid. As referred to herein, a conservative amino acid alteration is defined as one which does not significantly adversely affect biological activity and involves substitutions of the amino acid. The conservative amino acid that may be substituted for cysteine and methionine include at least: serine, alanine, glycine, valine, threonine, leucine, isoleucine, and tyrosine. More preferably they include serine and alanine. Most preferably, cysteine may be replaced with serine and methionine replaced with alanine.

Placental protein 14 is believed to exist in nature as a dimer of two identical, non-covalently linked protein subunits. Accordingly, since each subunit is believed to have the amino acid sequence shown in SEQ ID NO:1, a subunit of PP14 could be used as the therapeutic active substance for treating human immune system disorders according to the instant invention. The invention also encompasses use of subunits of PP14 that are covalently linked, either naturally or by artificial techniques known in the art.

In addition, it is contemplated that fragments of PP14 would be useful for treating human immune system disorders, provided that such fragments retained their therapeutic activity. Referring to SEQ ID NO:1, the protein fragment defined by amino acid residues 63 through 160 is believed to be a therapeutically active fragment of PP14 for purposes of the invention. This fragment includes four cysteine amino acids, which are believed to have biological activity. The fragment defined by amino acid residues 80 through 105 is also believed to be therapeutically active for purposes of the invention. The fragment defined by residues 80-105 is believed to be therapeutically active because: it is a linear sequence not involving disulfide bridges; the fragment contains a glycosylation site (at residues 85-87); the fragment has two tyrosine residues which, because of their phenyl side chains, may be involved in receptor interaction; and the double lysine sequence at residues 80-81 have double amino acid group activity, suggesting potential receptor activity.

The above-described forms of PP14 are used in an effective therapeutic amount, which will vary depending on the particular immune system disorder being treated, the method of administration, the form of PP14 utilized, and other factors understood to those having ordinary skill in the art. For example, treatment of arthritis may require direct injection of PP14 into the joints in order to achieve a suitable therapeutic dose, whereas a topically administered preparation for the treatment of psoriasis may require a different dosage of PP14. In general, one of ordinary skill in the art will be able to arrive at therapeutically effective dosages of PP14 for treatment of the various immune system disorders contemplated by the invention, based on the range of concentrations of PP14 which has been discovered to provide suitable in vitro activity, namely from about 0.1 to about 10 micromole/liter.

The activation of lymphocytes, resulting in cell proliferation, is a complex response mediated by a number of peptide messengers, the cytokines. At a simplified level, T-lymphocytes are activated by a sequential process. First, there is a requirement for the cytokine Interleukin-1 (IL-1) secreted by accessory cells (e.g., cells of the monocyte/macrophage lineage). In the presence of IL-1 the cytokine Interleukin-2 (IL-2) increases the expression of its own receptors, making the cell more responsive to IL-2—a positive feedback cycle. IL-2 also stimulates T-cell division (lymphoproliferation). Thus, the proliferation of T-cells requires the presence of both IL-1 and IL-2.

One approach to investigating the mode of action of lymphoproliferation with an inhibitor such as PP14 is to add an excess of cytokine along with the inhibitor and determine whether the suppression is reversed. One source of a crude mixture of cytokines is the supernatant taken from cultured activated lymphocytes. Such supernatants were demonstrated to reverse the suppressive action of PP14, indicating a mode of action relating to the secretion/activity of cytokines. The addition of recombinant IL-1 at a single dose significantly reduced the suppressive action of PP14 on lymphoproliferation, as shown in the following Table:

TABLE I

This Table shows the effect of the addition of 5 U/ml of recombinant IL-1 on the suppression of tritiated thymidine uptake by stimulated lymphocytes.

| Decidual sample no. | PP14 (ng/ml) | % suppression of 3H-Tdr | |
|---|---|---|---|
| | | +IL-1 | −IL-1 |
| DE A | 5.0 | 25 | 30 |
| DE B | 4.8 | 12 | 62 |
| DE C | 4.0 | 25 | 46 |
| DE D | 8.0 | 33 | 48 |
| DE E | 2.0 | 30 | 41 |

Mean (+/− S.D.)

These data indicate that PP14 may be operating via an IL-1-mediated mechanism.

To investigate this possibility further, peripheral blood mononuclear cells (a mixture primarily of T-cells and monocytes) were activated using the mitogen PHA in the presence and absence of inhibitory amounts of PP14. The amount of IL-1 released into the supernatants of the cultured cells was measured after different times of culture. The results from the two experiments carried out are shown in the attached Figure, and the data are given in Table 2 below. It can be seen that PP14 significantly inhibited the release of IL-1 into the supernatant by activated cells. These data on IL-1 strongly suggest that PP14 is acting at the IL-1 level of T-cell activation by inhibiting its synthesis/release.

TABLE 2

This Table shows the effect of PP14 in decidual extracts on the release into cell culture supernatants of IL-1 by stimulated peripheral blood lymphocytes.

| Experiment 1 | TIME (hours) | | | |
|---|---|---|---|---|
| | 22.5 | 41 | 65 | 89 |
| Unstimulated | 0.2 | 0.2 | 0.1 | 0.1 |
| Immunoabsorbed extract | 1.583 | 1.266 | 1.232 | 1.196 |
| Unabsorbed extract | 0.406 | 0.216 | 0.212 | 0.2 |
| % Suppression | 75% | 83% | 91% | 83% |

| Experiment 2 | TIME (hours) | | | |
|---|---|---|---|---|
| | 18 | 42 | 66 | 80 |
| Unstimulated | 0.6 | 0.2 | 0.4 | 0.3 |
| Immunoabsorbed extract | 1.789 | 2.554 | 2.709 | 2.807 |
| Unabsorbed extract | 0.7 | 1.162 | 1.630 | 1.967 |
| % Suppression | 61% | 55% | 40% | 30% |

NOTES
Unstimulated - spontaneous release of IL-1 from unstimulated lymphocytes.
Immunoabsorbed extract - IL-1 release from stimulated cells in the presence of a crude decidual extract from which PP14 had been specifically removed by monoclonal antibody immunoabsorption.
Unabsorbed extract - IL-1 release from stimulated lymphocytes in the presence of a crude decidual extract containing 8.0 ug/ml of PP14.
Percent suppression - the suppression of IL-1 released into the cell culture supernatants by PP14 in decidual extracts, expressed as a percent of the release of IL-1 in the presence of decidual extracts from which PP14 had been removed.

Individual results for each experiment are means of triplicate determinations.

A monoclonal antibody which specifically binds to PP14 has been isolated and characterized. This monoclonal antibody is designated MAb 14/1/1, and was derived from hybridomal cell lines produced by fusion, using a polyethylene glycol method of spleen cells from mice immunized with crude extracts of deciduum with the myeloma cell line P3/NS1/1-Ag4-1, which is a standard myeloma cell line. Clones secreting anti-PP14 were selected using the radiolabelled PP-14 used for the radioimmumoassay (BOLTON et at., 1983, supra). Positive cultures were cloned three times by limiting dilution and those yielding the highest titers used to induce tumors in Balb/C mice. IgG was isolated from ascitic fluid from ion exchange chromatography or affinity chromatography on protein -A.

The specificity of the antibody was examined in two ways. First, the two-site immunoradiometric assay was set up using a polyclonal extracting antibody and the monoclonal as labelled antibody. Polyclonal antibody, raised against crude decidual tissue extract, was covalently linked to Sepharose-4B by standard procedures. This was incubated in excess in the presence of standard PP14 or the potentially cross-reacting protein for two hours at room temperature. Subsequently, radioiodinated monoclonal antibody was added, incubated a further two hours, and the solid-coupled antibody washed and counted for radioactivity. This represents a conventional 2-site immunoradiometric assay. The cross-reaction of various decidual/placenta proteins was investigated in this system.

The following gave less than 0.1% cross reaction: hPL, SP1, pp5, pp12, pregnancy-associated plasma protein-A (PAPP-A), placental alkaline phosphatase, placental malic dehydrogenase, placental sphyngomyelinase, placental arylamidase, placental choline acetyltransferase, with only PP14 having any observed activity in this assay.

The other method involved investigating the binding to the monoclonal antibody of radioactively-labelled pure proteins. No significant binding of prolactin, hCG, or PAPP-A was detected. This antibody could be used in the assay, for example by a two-site immunoradiometric procedure, and purification of PP14. As previously mentioned, the details of the radioimmunoassay for PP14 are disclosed in the 1983 BOLTON et al. article, identified above.

The following examples are given to illustrate the invention, but are not deemed to be limiting thereof.

Example 1

Evidence that PP14 inhibits IL-1 release

Method 1—the mitogenic response of human lymphocytes

Human peripheral blood lymphocytes proliferate in response to stimulation by the mitogen phytohaemagglutinin (PHA), the proliferation being measured by the incorporation of tritiated thymidine into the DNA of the dividing cells. This is a standard test of lymphocyte responsiveness. PP14 inhibits lymphocyte proliferation in response to PHA stimulation. The addition of recombinant IL-1 partially reverses the inhibition caused by PP14.

The test system used in this example was to investigate the effect of recombinant IL-1 on the mitogen-induced stimulation of PP14-inhibited peripheral blood lymphocytes. The use of PP14-inhibited cells in experiments such as this is unique methodology.

The PP14 inhibition of cells in this example was carried out as follows. Cells were treated with crude extracts of human decidual tissue in which the PP14 concentration was measured by radioimmunoassay. As a control for each treated cell preparation, a portion of the cells were treated with the same extract that had been immunoabsorbed using a monoclonal antibody to PP14, MAb/PP14/1/1, to remove the PP14 in a highly specific manner. The difference between the activity of the cells treated with these two preparations represented the effect of PP14. Thus, the effects measured were those of PP14, which specifically binds to this monoclonal antibody.

Peripheral blood mononuclear cells were isolated from whole blood obtained from healthy donors by a standard density gradient centrifugation method. After washing in a physiological medium, the cells were resuspended at an appropriate concentration of viable cells and incubated in the presence of the PP14 preparation and the mitogen at a stimulatory concentration.

The effects of IL-1, or other test compound, were assessed by inclusion at appropriate concentrations in this incubation, including also the necessary controls. The cells were incubated for 72 hours at 37° C. in an atmosphere of 5% carbon dioxide and 100% humidity under sterile conditions. Six hours prior to termination of the cultures, the cells were pulsed with 1 uCi of tritiated thymidine, and on termination the cells were harvested automatically onto glass fiber filters.

The degree of lymphoproliferation was assessed by measuring the incorporation of tritiated thymidine into the harvested cells by liquid scintillation counting. Inhibition of tritiated thymidine uptake by pp14, and the effect of IL-1 were as follows:

| % inhibition of tritiated thymidine uptake | |
|---|---|
| Without IL-1 | With 5 U/ml IL-1 |
| 45.4 +/− 11.6 | 25.0 +/− 8.0 |

These are mean results from 15 different experiments, each performed in triplicate, using 5 different decidual extracts as the source of PP14 and cells from 2 separate donors. The results are significantly different (p<0.0001), indicating a significant reversal of the inhibitory effect of PP14 on lymphoproliferation by IL-1.

Example 2

The effect of PP14 on the production of IL-1 by stimulated peripheral blood mononuclear cells Peripheral blood mononuclear cells, as isolated by density gradient centrifugation, contain not only lymphocytes (the majority of cells present) but also monocyte/macrophages, which are necessary accessory cells in the lymphoproliferative reaction described above. It is this latter cell type which synthesizes and secretes IL-1. These cells can be activated to secrete their specific products which include IL-1 by both mitogens (e.g., PHA) and lipopolysaccharide (LPS).

The test system used in this example was to investigate the production of macrophage/monocyte products released from stimulated PP14-inhibited peripheral blood mononuclear cell preparations, measuring the products by commercially available immunoassay systems. The use of PP14-inhibition of cells was carried out as in Method 1 of Example 1 above, which again is unique methodology.

Peripheral blood mononuclear cells were prepared as under Method 1. Appropriate numbers of cells were incubated in the presence of the PP14 preparation and the stimulator for various times under the conditions described above. At the termination of the culture period the cells were harvested and the supernatants assayed for IL-1 and Tumour Necrosis Factor (TNF), both known to be products of macrophage/monocyte cells. Typical results are summarized below. Inhibition of IL-1 release by stimulated peripheral mononuclear cells by PP14:

| % inhibition of IL-1 release | |
|---|---|
| PHA stimulated cells | LPS stimulated cells |
| 82.5 | 67.0 |

These are mean results from 3 experiments.

This inhibition of IL-1 release from stimulated (using either PHA or LPS) mononuclear cells by PP14 is dose dependant, as shown in the Figure, wherein· represents cells stimulated with mitogen (PHA) and ◯ represents cells stimulated with LPS.

Example 3

Comparison of IL-1 and TNF production by PP14-inhibited stimulated peripheral blood mononuclear cells:

| | Cells stimulated with mitogen: | |
|---|---|---|
| | IL-1 produced | TNF produced |
| stimulated control | 2.60 ng/ml | 1043 pg/ml |
| +PP14 (4 ug/l) | 0.46 ng/ml | 1474 pg/ml |

The invention being thus described, it will be obvious that the same may be varied in many ways. Such variations are not to be regarded as a departure from the spirit and scope of the invention and all such modifications are intended to be included within the scope of the claims.

What is claimed is:

1. A method for treating an immune system disorder in a human by administering to said human a therapeutically effective amount of an active substance selected from the group consisting of muteins of PP14, fragments of PP14, and subunits of PP14, to alleviate said immune system disorder, where said members retain the therapeutic activity of the unmodified PP14.

2. The method of claim 1, wherein said derivatives of PP14 comprise PP14 augmented by a least one additional molecule selected from the group consisting of glucose moieties, lipids, phosphate groups, acetyl groups, hydroxyl groups, saccharides, methyl groups, propyl groups, amino acids, and polymeric molecules.

3. The method of claim 1, wherein said derivatives of PP14 comprise PP14 having at least one amino acid residue that has been modified by oxidation or reduction.

4. The method of claim 1, wherein the PP14 comprises a dimer of two non-covalently linked protein subunits.

5. The method of claim 4, wherein at least one of said subunits is employed as the active substance administered for said treatment.

6. The method of claim 5, wherein the subunit has the nucleotide and amino acid sequence shown in SEQ ID NO:1.

7. The method of claim 1, wherein the PP14 comprises two covalently linked protein subunits, wherein each of the subunits has the nucleotide and amino acid sequence shown in SEQ ID NO:1.

8. The method of claim 1, wherein said fragment of PP14 has the nucleotide and amino acid sequence of residues 63 through 160 of SEQ ID NO:1.

9. The method of claim 1, wherein said fragment has the nucleotide and amino acid sequence of residues 80 through 105 of SEQ ID NO:1.

10. The method of claim 1, wherein said immune system disorder is selected from the group consisting of allergic conditions, autoimmune conditions, and inflammatory conditions.

11. The method of claim 10, wherein said active substance is administered by a method selected from the group consisting of intravenous injection, intramuscular injection, oral administration, topical administration, rectal administration, and inhalation.

12. The method of claim 10, wherein said active substance is obtained from a source selected from the group consisting of mammalian placenta, mammalian blood, amniotic fluid, seminal plasma, cells in tissue culture, decidual cells, decidual organs, endometrial cells, endometrial organs, and sources containing eukaryotic or prokaryotic cells engineered to express PP14, muteins of PP14, fragments of pp14 or subunits of PP14.

13. The method of claim 10, wherein said immune system disorder is selected from the group consisting of arthritis, rheumatoid arthritis, asthma, graft-versus-host disease, organ rejection, systemic lupus erythematosis, atopic allergy, inflammatory bowel disease, multiple sclerosis, and allergic dermatitis.

14. The method of claim 13, wherein said autoimmune conditions are manifested by infertility.

15. The method of claim 13, wherein said substance is administered in admixture with a pharmaceutically acceptable carrier.

16. The method of claim 1, wherein said immune system disorder comprises a lymphoproliferative disorder.

17. The method of claim 16, wherein said lymphoproliferative disorder is selected from the group consisting of malignant non-Hodgkin's lymphoma, Hodgkin's disease, and malignant histiocytosis.

18. The method of claim 1, wherein said immune system disorder is a neoplastic disorder.

19. The method of claim 18, wherein said neoplastic disorder is a leukemia.

20. The method of claim 1, wherein said immune system disorder is a disorder resulting from the presence in said human of the virus which causes acquired immunodeficiency syndrome.

21. A method for treating an immune system disorder in a human by administering to said human a therapeutically effective amount of monoclonal antibodies directed agains a substance selected from the group consisting of derivatives of PP14, muteins of PP14, fragments of PP14, and subunits of PP14, wherein said members retain the therapeutic activity of the unmodified PP14.

22. The method of claim 21, wherein said immune system disorder is a disorder resulting from the presence in said human of the virus which causes acquired immunodeficiency syndrome.

23. The method of claim 21, wherein said monoclonal antibodies are administered by a method selected from the group consisting of intravenous injection, intramuscular injection, oral administration, topical administration, rectal administration, adn inhalation.

24. The method of claim 21, wherein said monoclonal antibodies are administered in admixture with a pharmaceutically acceptable carrier.

25. A method for inhibiting Interleukin-1 production in a human, which comprises: administering to said human a therapeutically effective amount of an active substance selected from the group consisting derivatives of PP14, muteins of PP14, fragments of PP14, and subunits of PP14, in an amount effective to inhibit said Interleukin-1 production, wherein said member retain the therapeutic activity of the unmodified PP14.

26. The method of claim 25, wherein said active substance is administered by means selected from the group consisting of intravenous injection, intramuscular injection, oral administration, topical administration, rectal administration, and inhalation.

27. The method of claim 25, wherein said active substance is obtained from a source selected from the group consisting of mammalian placenta, mammalian blood, amniotic fluid, seminal plasma, cells in tissue culture, decidual cells, decidual organs, endometrial cells, endometrial organs, and sources containing eukaryotic cells or prokaryotic cells engineered to express PP14, muteins of PP14, fragments of PP14 or subunits of PP14.

28. The method of claim 25, wherein said active substance is administered in admixture with a pharmaceutically acceptable carrier.

* * * * *

UNITED STATES PATENT AND TRADEMARK OFFICE
CERTIFICATE OF CORRECTION

PATENT NO. : 5,256,411
DATED : October 26, 1993
INVENTOR(S) : Anthony E. BOLTON and Alan DRIZEN It is certified that error appears in the above-identified patent and that said Letters Patent is hereby corrected as shown below:

In Column 15, line 23, "where" should read --wherein--.

In Column 16, line 62, "adn" should read --and--.

In Column 17, line 1, after "from the group consisting", insert --of--.

In Column 17, line 4, "wherein said member" should read --wherein said members--.

Signed and Sealed this

Twenty-sixth Day of April, 1994

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 819 base pairs
        ( B ) TYPE: nucleic acid -continued

```
           ( C ) STRANDEDNESS: double stranded
           ( D ) TOPOLOGY: linear ( x ) PUBLICATION INFORMATION:
           ( A ) AUTHORS: Julkunen, Mervi
                          Seppl, Markku
                          J nne, Olli A.
           ( B ) TITLE: Complete Amino Acid Sequence of Human
                          Placental Protein 14: A Progesterone-
                          Regulated Uterine Protein Homologous To
                          a- Lactoglobulins
           ( C ) JOURNAL: Proc. Natl. Acad. Sci. USA
           ( D ) VOLUME: 85
           ( F ) PAGES: 8845-8849
           ( G ) DATE: DEC-1988
           ( K ) RELEVANT RESIDUES IN SEQ ID NO:1: FROM 1 to 819

( x i ) SEQUENCE DESCRIPTION: SEQ ID NO:1:
```

| | | | | | | | | | | |
|---|---|---|---|---|---|---|---|---|---|---|
| CATCCCTCTG | GCTCCAGAGC | TCAGAGCCAC | CCACAGCCGC | AGCC | | | | | | 44 |
| ATG | CTG | TGC | CTC | CTG | CTC | ACC | CTG | GGC | GTG | GCC | 77 |
| Met | Leu | Cys | Leu | Leu | Leu | Thr | Leu | Gly | Val | Ala | |
| -18 | | | | | | | -10 | | | | |
| CTG | GTC | TGT | GGT | GTC | CCG | GCC | ATG | GAC | ATC | CCC | 110 |
| Leu | Val | Cys | Gly | Val | Pro | Ala | Met | Asp | Ile | Pro | |
| | | | | | | | 1 | | | | |
| CAG | ACC | AAG | CAG | GAC | CTG | GAG | CTC | CCA | AAG | TTG | 143 |
| Gln | Thr | Lys | Gln | Asp | Leu | Glu | Leu | Pro | Lys | Leu | |
| | | | | | 10 | | | | | | |
| GCA | GGG | ACC | TGG | CAC | TCC | ATG | GCC | ATG | GCG | ACC | 176 |
| Ala | Gly | Thr | Trp | His | Ser | Met | Ala | Met | Ala | Thr | |
| | | | | | 20 | | | | | | |
| AAC | AAC | ATC | TCC | CTC | ATG | GCG | ACA | CTG | AAG | GCC | 209 |
| Asn | Asn | Ile | Ser | Leu | Met | Ala | Thr | Leu | Lys | Ala | |
| | | | 30 | | | | | | | | |
| CCT | CTG | AGG | GTC | CAC | ATC | ACC | TCA | CTG | TTG | CCC | 242 |
| Pro | Leu | Arg | Val | His | Ile | Thr | Ser | Leu | Leu | Pro | |
| | | 40 | | | | | | | | | |
| ACC | CCC | GAG | GAC | AAC | CTG | GAG | ATC | GTT | CTG | CAC | 275 |
| Thr | Pro | Glu | Asp | Asn | Leu | Glu | Ile | Val | Leu | His | |
| | 50 | | | | | | | | | | |
| AGA | TGG | GAG | AAC | AAC | AGC | TGT | GTT | GAG | AAG | AAG | 308 |
| Arg | Trp | Glu | Asn | Asn | Ser | Cys | Val | Glu | Lys | Lys | |
| 60 | | | | | | | | | | 70 | |
| GTC | CTT | GGA | GAG | AAG | ACT | GGG | AAT | CCA | AAG | AAG | 341 |
| Val | Leu | Gly | Glu | Lys | Thr | Gly | Asn | Pro | Lys | Lys | |
| | | | | | | | | | 80 | | |
| TTC | AAG | ATC | AAC | TAT | ACG | GTG | GCG | AAC | GAG | GCC | 374 |
| Phe | Lys | Ile | Asn | Tyr | Thr | Val | Ala | Asn | Glu | Ala | |
| | | | | | | | | 90 | | | |
| ACG | CTG | CTC | GAT | ACT | GAC | TAC | GAC | AAT | TTC | CTG | 407 |
| Thr | Leu | Leu | Asp | Thr | Asp | Tyr | Asp | Asn | Phe | Leu | |
| | | | | | | | 100 | | | | |
| TTT | CTC | TGC | CTA | CAG | GAC | ACC | ACC | ACC | CCC | ATC | 440 |
| Phe | Leu | Cys | Leu | Gln | Asp | Thr | Thr | Thr | Pro | Ile | |
| | | | | | | 110 | | | | | |
| CAG | AGC | ATG | ATG | TGC | CAG | TAC | CTG | GCC | AGA | GTC | 473 |
| Gln | Ser | Met | Met | Cys | Gln | Tyr | Leu | Ala | Arg | Val | |
| | | | | | 120 | | | | | | |
| CTG | GTG | GAG | GAC | GAT | GAG | ATC | ATG | CAG | GGA | TTC | 506 |
| Leu | Val | Glu | Asp | Asp | Glu | Ile | Met | Gln | Gly | Phe | |
| | | | | 130 | | | | | | | |
| ATC | AGG | GCT | TTC | AGG | CCC | CTG | CCC | AGG | CAC | CTA | 539 |
| Ile | Arg | Ala | Phe | Arg | Pro | Leu | Pro | Arg | His | Leu | |
| | | | 140 | | | | | | | | |
| TGG | TAC | TTG | CTG | GAC | TTG | AAA | CAG | ATG | GAA | GAG | 572 |

-continued

| Trp | Tyr | Leu | Leu<br>150 | Asp | Leu | Lys | Gln | Met | Glu | Glu | |
|---|---|---|---|---|---|---|---|---|---|---|---|
| CCG<br>Pro | TGC<br>Cys<br>160 | CGT<br>Arg | TTC<br>Phe<br>162 | TAG<br>AM | CTCACCTCCG | CCTCCAGGAA | | | | | 607 |

| GACCAGACTC | CCACCCTTCC | ACACCTCCAG | AGCAGTGGGA | CTTCCTCCTG | 657 |
|---|---|---|---|---|---|
| CCCTTTCAAA | GAATAACCAC | AGCTCAGAAG | ACGATGACGT | GGTCATCTGT | 707 |
| GTCGCCATCC | CCTTCCTGCT | GCACACCTGC | ACCATTGCCA | TGGGGAGGCT | 757 |
| GCTCCCTGGG | GGCAGAGTCT | CTGGCAGAGG | TTATTAATAA | ACCCTTGGAG | 807 |
| CATGAAAAAA | AA | | | | 819 |